(12) United States Patent
Lin

(10) Patent No.: US 8,181,554 B2
(45) Date of Patent: May 22, 2012

(54) EYEBROW EMBROIDERY MACHINE

(75) Inventor: Su-Lin Lin, Taipei (TW)

(73) Assignee: Mei-Chi-Na Hsinyen Co., Ltd., Taipei (TW)

( * ) Notice: Subject to any disclaimer, the term of this patent is extended or adjusted under 35 U.S.C. 154(b) by 372 days.

(21) Appl. No.: 12/461,973

(22) Filed: Aug. 31, 2009

(65) Prior Publication Data

US 2011/0048174 A1 Mar. 3, 2011

(51) Int. Cl.
*B43K 5/00* (2006.01)
(52) U.S. Cl. .............................. 81/9.22; 30/366; 606/186
(58) Field of Classification Search ................... 81/9.22; 606/185–186; 30/366
See application file for complete search history.

(56) References Cited

U.S. PATENT DOCUMENTS

| 5,279,552 | A | * | 1/1994 | Magnet | 604/47 |
| 6,505,530 | B2 | * | 1/2003 | Adler et al. | 81/9.22 |
| 2010/0036317 | A1 | * | 2/2010 | Oginski et al. | 604/131 |
| 2010/0063356 | A1 | * | 3/2010 | Smith | 600/114 |

* cited by examiner

*Primary Examiner* — Debra S Meislin
(74) *Attorney, Agent, or Firm* — Bacon & Thomas, PLLC

(57) ABSTRACT

An eyebrow embroidery machine includes a connecting sleeve, an eyebrow embroidery bushing, an anti-backflow plastic cover, an eyebrow embroidery needle module and a transmission mechanism. At least one circular flange is formed at an end of the eyebrow embroidery bushing and embedded into another end of the connecting sleeve. An end of the anti-backflow plastic cover is fixed onto the periphery of the eyebrow embroidery needle module and another end is connected to the connecting sleeve. The eyebrow embroidery needle module installed in the connecting sleeve includes a core link rod at an end and an eyebrow embroidery needle at another end and passed out of the eyebrow embroidery bushing. The transmission mechanism is screwed with the connecting sleeve, and provided for moving the core link rod, the anti-backflow plastic cover and the eyebrow embroidery needle reciprocally along the central axis of the eyebrow embroidery machine.

7 Claims, 3 Drawing Sheets

EYEBROW EMBROIDERY MACHINE

FIELD OF THE INVENTION

The present invention relates to an eyebrow embroidery machine, in particular to an eyebrow embroidery machine with an anti-backflow and anti-leakage design to prevent any dye attached onto the eyebrow embroidery machine from flowing back to a motor of the eyebrow embroidery machine or leaking from the eyebrow embroidery machine by a capillary action to cause a short circuit or contaminate an operator's hand, when the eyebrow embroidery machine is placed horizontally.

BACKGROUND OF THE INVENTION

Most conventional eyebrow embroidery machines are composed of a transmission mechanism and a needle mechanism, and the transmission mechanism can drive an eyebrow embroidery needle in the needle mechanism to move reciprocally along the central axis of the eyebrow embroidery machine, such that an eyebrow embroidery operator can attach a liquid dye at the tip of the eyebrow embroidery needle to form a predetermined tattoo on a human body, and discard the eyebrow embroidery needle used after the embroidery job, and another brand new eyebrow embroidery needle is used for the next embroidery job to assure a sanitary usage and prevent blood-borne infectious diseases. However, the aforementioned needle mechanism generally includes a bushing and an eyebrow embroidery needle, and the needle head of the eyebrow embroidery needle is passed through the bushing and exposed to the outside from the bushing, and thus the dye adhered onto the eyebrow embroidery needle before the embroidery job takes place or the blood adhered onto the eyebrow embroidery needle before the embroidery job finishes is generally carried into the bushing, since the eyebrow embroidery needle is moved continuously back and forth. In the meantime, the dye or blood attached onto the internal wall surface of the bushing flows back into the motor along the internal wall surface of the bushing due to the capillary action, and causes an electric short circuit. The dye at the needle head may flow back into the bushing to contaminate the motor, if an operator places the eyebrow embroidery machine horizontally during the embroidery job. Thus, related cosmetic manufacturers generally design an eyebrow embroidery machine with an anti-backflow structure to avoid the aforementioned problems.

In FIG. 1, an eyebrow embroidery machine 1 comprises a transmission mechanism 11 and a needle mechanism 13, wherein the transmission mechanism 11 includes a motor 111, and the motor 111 includes a transmission shaft 113 and drives the transmission shaft 113 to displace along the central axis of the eyebrow embroidery machine. The transmission mechanism 11 further includes a power cord 115 connected to an end away from the transmission shaft 113 for supplying electric power required for the operation of the motor 111. The needle mechanism 13 further includes a connecting sleeve 131, an eyebrow embroidery bushing 133, a needle bushing 135, an anti-backflow plastic cover 136 and an eyebrow embroidery needle 137, wherein an end of the connecting sleeve 131 is coupled to an end of the transmission mechanism 11, and another end of the connecting sleeve 131 is screwed to an end of the eyebrow embroidery bushing 133, and an end of the anti-backflow plastic cover 136 is sheathed onto the periphery of the needle bushing 135, and another end is clamped between an end of the transmission mechanism 11 and the connecting sleeve 131, and the needle bushing 135 is installed in the connecting sleeve 131. In addition, an end of the needle bushing 135 is screwed with the transmission shaft 113 of the transmission mechanism 11, and another end of the needle bushing 135 is inserted with the eyebrow embroidery needle 137, and the eyebrow embroidery needle 137 extends to the outside from another end of the eyebrow embroidery bushing 133 and is capable of attaching a liquid dye, so that the dye or blood flowing back into the eyebrow embroidery bushing 133 will be blocked by the anti-backflow plastic cover 136 and cannot flow into the transmission mechanism 11, so as to prevent a short circuit of the motor 111 installed in the transmission mechanism 11 or a contamination of the transmission shaft 113. However, when the eyebrow embroidery machine 1 is used, other problems may occur. In FIG. 1, the dye or blood flowing back into the eyebrow embroidery bushing 133 is blocked by the anti-backflow plastic cover 136, but the dye or blood may be accumulated at the screwed position (as indicated by the dotted circle A in FIG. 1) between the connecting sleeve 131 and the eyebrow embroidery bushing 133. Particularly, if an operator places the eyebrow embroidery machine 1 in a horizontal position, the aforementioned situation may occur easily. In general, two adjacent screw threads in a screw threaded structure are not arranged closely adjacent with each other, but a gap exists between any two adjacent screw threads, such that the dye or blood accumulated at the screwed position between the connecting sleeve 131 and the eyebrow embroidery bushing 133 will leak from the gap between the screw threads and flow to the external periphery of the eyebrow embroidery bushing 133. Particularly, when the operator turns the eyebrow embroidery bushing 133 to adjust the length of the needle head exposed from the eyebrow embroidery needle, the speed of the leakage and the flow of the dye will be increased, resulting in the inconvenience of holding the eyebrow embroidery machine and the contamination to the operator's hand that ruins the product image and hygiene of the eyebrow embroidery machine.

In FIG. 1, the transmission mechanism 11 and the needle mechanism 13 are connected by screwing the connecting sleeve 131 with the transmission mechanism 11, as well as screwing the needle bushing 135 with the transmission shaft 113, such that when the operator changes the needle mechanism 13, the operator has to align the transmission shaft 113 and the needle bushing 135 at the corresponding screwed position precisely before the transmission mechanism 11 and the needle mechanism 13 can be installed successfully. Since the needle bushing 135 is smaller, therefore the operator may shift from the predetermined screwed position, which makes the installation more difficult and inconvenient, and results in a longer waiting time before having an eyebrow embroidery service. Obviously, the conventional eyebrow embroidery machine still has problems in its use and installation. Therefore, it is an important subject for related cosmetic manufacturers to design and develop an eyebrow embroidery machine to achieve the effects of overcoming the shortcomings of the prior art, and preventing the dye from flowing back into the motor or leaking from the external periphery of the eyebrow embroidery bushing, so as to facilitate the operator's installation.

SUMMARY OF THE INVENTION

In view of the aforementioned shortcomings of the conventional eyebrow embroidery machine, the inventor of the present invention based on years of experience in the related industry to conduct extensive researches and experiments, and finally developed an eyebrow embroidery machine in accordance with the present invention to overcome the shortcomings of the prior art.

Therefore, it is a primary objective of the present invention to provide an eyebrow embroidery machine to prevent the dye or blood from flowing back into a circuit of the eyebrow embroidery machine or leaking from the external periphery of the eyebrow embroidery machine. The eyebrow embroidery machine comprises a connecting sleeve, an eyebrow embroidery needle module, an eyebrow embroidery bushing and a transmission mechanism, wherein an internal screw thread is formed inside an end of the connecting sleeve, and a protruding rib is formed inside the connecting sleeve and proximate to the internal screw thread, and the anti-backflow plastic cover is made of an elastic material, and has an end sheathed and fixed onto the periphery of the eyebrow embroidery needle module and a flange at another end attached closely to the protruding rib and proximate to a side of the internal screw thread, and the eyebrow embroidery needle module is installed in the connecting sleeve. The eyebrow embroidery needle module further includes a needle bushing with a substantially H-shaped axial cross-section, and the needle bushing has a core link rod installed at an end proximate to the internal screw thread and an eyebrow embroidery needle installed at another end. At least one circular flange is disposed around the external periphery of an end of the eyebrow embroidery bushing, and an end of the circular flange is embedded into another end of the connecting sleeve, such that the circular flange can be attached to an internal wall surface of the connecting sleeve watertightly, and the eyebrow embroidery needle passes through the eyebrow embroidery bushing and extends to the outside from another end of the eyebrow embroidery bushing, such that the operator can adhere a liquid dye onto a needle head. A power cord is connected to an end of the transmission mechanism for supplying electric power required for the operation of a motor, and an external screw thread is formed at another end for screwing and connecting the internal screw thread of the connecting sleeve. A transmission rod of the motor is connected to an end of the core link rod and is driven by the motor to move the core link rod, the anti-backflow plastic cover and the eyebrow embroidery needle along the central axis of the eyebrow embroidery machine reciprocally, so that the structure of the needle bushing of the present invention can prevent the dye adhered onto the eyebrow embroidery needle from flowing back into the needle bushing due to a capillary action, and the dye will not flow back into the core link rod. With the circular flange formed at the eyebrow embroidery bushing, the dye in the eyebrow embroidery bushing can be prevented from leaking out of the eyebrow embroidery bushing or contaminating the operator's hand that affects the product image of the eyebrow embroidery machine.

Another objective of the present invention is to install provide a first magnet at an end of the transmission rod and a second magnet at an end of the core link rod, and the magnets will attract each other, so that when an operator screws the transmission mechanism with an assembled connecting sleeve, the attraction of the magnets can connect the transmission rod and the core link rod quickly to improve the assembling efficiency.

DETAILED DESCRIPTION OF THE PREFERRED EMBODIMENTS

Figure 1:
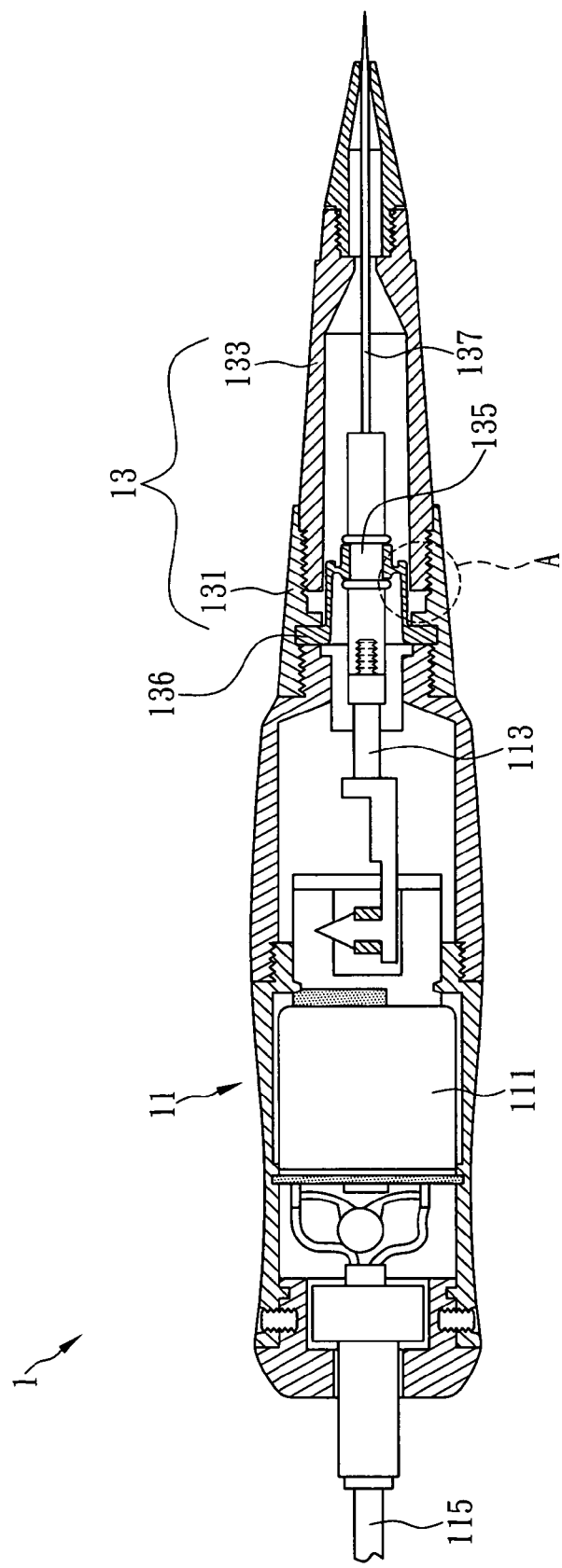
FIG. 1 is a cross-sectional view of a conventional eyebrow embroidery machine.
Figure 2:
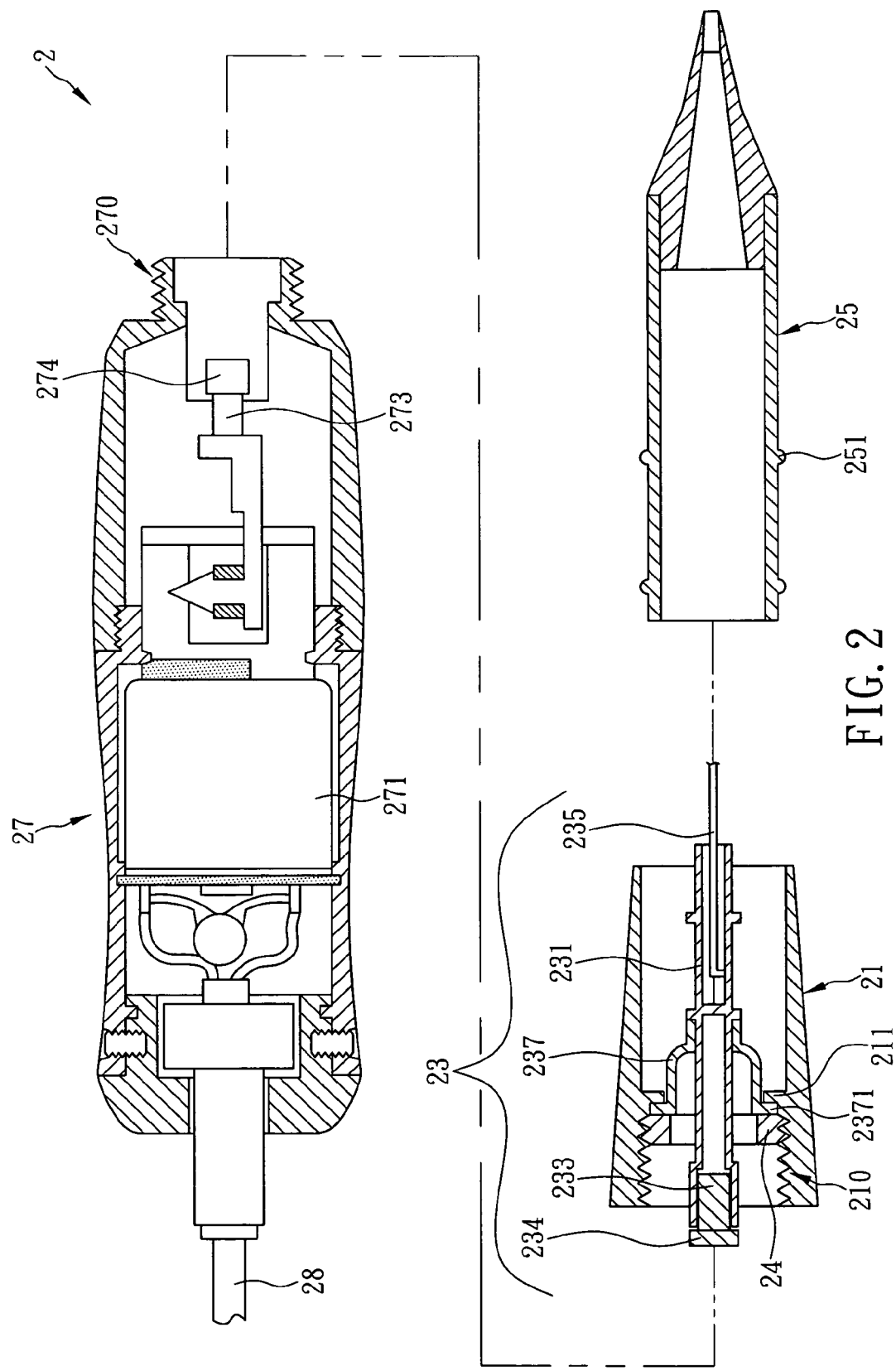
FIG. 2 is an exploded view of an eyebrow embroidery machine of the present invention.
Figure 3:
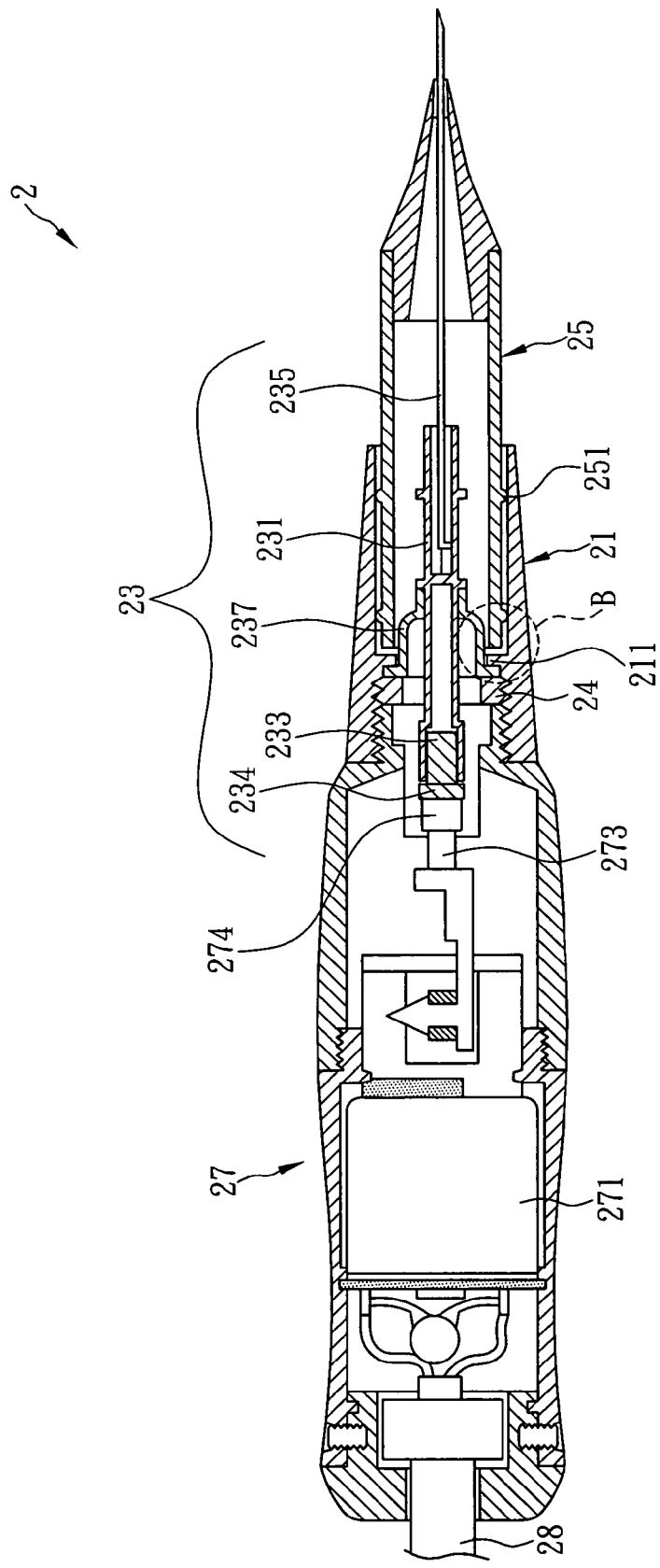
FIG. 3 is an exploded view of an eyebrow embroidery machine of the present invention.

The present invention discloses an eyebrow embroidery machine that changes a portion of the structure of a conventional eyebrow embroidery machine to overcome the aforementioned problems and achieve the effects of a better anti-backflow, a better anti-leakage and an easy installation. With reference to FIGS. 2 and 3, the eyebrow embroidery machine 2 comprises a connecting sleeve 21, an eyebrow embroidery needle module 23, a watertight O-ring 24, an eyebrow embroidery bushing 25 and a transmission mechanism 27, wherein the connecting sleeve 21 contains a penetrating containing space, an internal screw thread 210 formed on an internal side of an end of the connecting sleeve 21, and a protruding rib 211 formed at a position proximate to the internal screw thread 210. In addition, at least one circular flange 251 is formed at an external periphery of an end of the eyebrow embroidery bushing 25, wherein the circular flange 251 is integrally formed with the eyebrow embroidery bushing 25 or a standalone circular flange 251 is sheathed or attached onto the eyebrow embroidery bushing 25 individually. When an end of the eyebrow embroidery bushing 25 is embedded or inserted into another end of the connecting sleeve 21, the circular flange 251 will be pressed and abutted against the connecting sleeve 21 watertightly, such that a relatively large frictional force is produced between the circular flange 251 and an internal wall surface of the connecting sleeve 21, and the eyebrow embroidery bushing 25 will not be separated from the connecting sleeve 21 easily by vibrations. If an operator applies a large force, the operator can adjust the position of the circular flange 251 with respect to the connecting sleeve 21. The eyebrow embroidery needle module 23 further includes a needle bushing 231 having a substantially H-shaped axial cross-section for partitioning the needle bushing 231 into two independent containing spaces, and an anti-backflow plastic cover 237 sheathed onto the external periphery of the needle bushing 231, wherein the anti-backflow plastic cover 237 is made of an elastic material and has an end fixed onto the needle bushing 231 and another end extended towards the internal screw thread 210, such that a flange 2371 at another end is attached closely with the protruding rib 211 and proximate to a side of the internal screw thread 210 to install the eyebrow embroidery needle module 23 in the connecting sleeve 21, and the dye flowing back into the connecting sleeve 21 is blocked by the anti-backflow plastic cover 237 to prevent any backflow of the dye into the internal screw thread 210.

With reference to FIGS. 2 and 3, the needle bushing 231 includes a core link rod 233 installed in a containing space proximate to an end of the internal screw thread 210, and an eyebrow embroidery needle 235 installed at a containing space proximate to another end of the internal screw thread 210, and a needle head of the eyebrow embroidery needle 235 is passed through the eyebrow embroidery bushing 25 and exposed from another end of the eyebrow embroidery bushing 25, such that an operator can attach a liquid dye onto the needle head. Since the containing spaces of the needle bushing 231 are isolated, therefore the dye adhered onto the needle head of the eyebrow embroidery needle 235 will not flow back into the needle bushing 231 due to the capillary action, but will simply stay in the containing space at another end of the needle bushing 231. The dye will be unable to flow back or touch the core link rod 233. In other words, the structure of the needle bushing 231 in accordance with the present invention can block a portion of the dye at the another end of the needle bushing 231 effectively. In addition, the watertight O-ring 24 is screwed and engaged with an end of the connecting sleeve 21 through the internal screw thread 210 and attached closed to abut a flange 2371 at another end of the anti-backflow plastic cover 237, such that the flange 2371 at the another end of the anti-backflow plastic cover 237 can be installed between the watertight O-ring 2 and the protruding rib 211 watertightly, such that the dye will not leak from the another end of the anti-backflow plastic cover 237 easily or flow back to the internal screw thread 210. With the structure of the needle bushing 231 and the compression of the watertight O-ring 24 in accordance with the present invention, the dye or blood entering into the connecting sleeve 21 can be blocked at the another end of the connecting sleeve 21 effectively, so that the dye entering into the eyebrow embroidery bushing 25 and flowing back to an end of the eyebrow embroidery bushing 25 is blocked by the watertight O-ring 24 and accumulated at a position (as indicated by the dotted circle B in FIG. 3) proximate to the protruding rib 211. Since the circular flange 251 and an internal wall surface of the connecting sleeve 21 are attached watertightly, therefore the liquid dye cannot be leaked from the external periphery of the eyebrow embroidery bushing 25 to maintain the external periphery of the eyebrow embroidery bushing 25 clean and avoid contaminating the operator's hand that holds the eyebrow embroidery machine 2, and thus the aforementioned components (including the connecting sleeve 21, eyebrow embroidery needle module 23, watertight O-ring 24, and eyebrow embroidery bushing 25) can be assembled to form the needle mechanism.

In FIGS. 2 and 3, a power cord 28 is connected to an end of the transmission mechanism 27 for supplying electric power through the power cord 28, and a motor 271 installed in the transmission mechanism 27 includes a transmission rod 273 extended into another end of the transmission mechanism 27. When the motor 271 is turned on, the transmission rod 273 is driven to move the transmission rod 273 reciprocally back and forth along the central axis of the eyebrow embroidery machine 2. In addition, an external screw thread 270 formed at the another end of the transmission mechanism 27 can be screwed with the internal screw thread 210 of the connecting sleeve 21, such that the watertight O-ring 24 and the flange 2371 at the another end of the anti-backflow plastic cover 237 are forcedly pressed between the protruding rib 211 and an end of the transmission mechanism 27 to define a watertight status, and an end of the transmission rod 273 is connected to an end of the core link rod 233. When the transmission rod 273 is driven by the motor 271, the core link rod 233, the needle bushing 231, the anti-backflow plastic cover 237 and the eyebrow embroidery needle 235 can be moved reciprocally along the central axis of the eyebrow embroidery machine 2. However, other embodiments of the present invention may not include the watertight O-ring, but just forcedly press an end of the anti-backflow plastic cover after the transmission mechanism is screwed with the connecting sleeve.

With reference to FIGS. 2 and 3, a first magnet 274 is installed at an end of the transmission rod 273 and a second magnet 234 is installed at an end of the core link rod 233, such that the first magnet 274 and the second magnet 234 can be attracted with each other to improve the efficiency of installing the transmission mechanism 27 with the needle mechanism. When an operator screws the transmission mechanism 27 and the connecting sleeve 21, the first magnet 274 and the second magnet 234 will attract each other automatically, so that the transmission rod 273 can be connected to the core link rod 233, and the operator no longer needs to align the transmission rod 273 with the core link rod 233 precisely anymore, and the operator can complete the installation quickly and securely to reduce the installation time and improve the convenience of the installation effectively. In other preferred embodiments of the present invention, only one component is a magnet and the other component is a metal piece (such as an iron nugget), instead of installing both magnets between the transmission rod and the core link rod. In summation, if the eyebrow embroidery machine of the present invention is turned on, the dye or blood adhered onto the eyebrow embroidery needle 235 can be blocked and prevented from flowing back into the needle bushing 231 or the eyebrow embroidery bushing 25 due to the capillary action, and the dye or blood cannot flow back to an end of the connecting sleeve 21. In other words, the dye or blood will not touch the motor 271 to cause a possible short circuit. The dye or blood flowing back into the eyebrow embroidery bushing 25 can be blocked by the circular flange 251 and cannot leak from the external periphery of an end of the eyebrow embroidery bushing or contaminate the operator's hand 25 to affect the product image of the eyebrow embroidery machine.

While the invention has been described by means of specific embodiments, numerous modifications and variations could be made thereto by those skilled in the art without departing from the scope and spirit of the invention set forth in the claims.

What is claimed is:

1. An eyebrow embroidery machine, comprising:
a connecting sleeve, having an internal screw thread formed inside an end of the connecting sleeve, and a protruding rib formed inside the connecting sleeve at a position proximate to the internal screw thread;
an eyebrow embroidery bushing, having at least one circular flange formed at an external periphery of an end of the eyebrow embroidery bushing, and the eyebrow embroidery bushing being watertightly embedded into another end of the connecting sleeve at a position corresponding to the circular flange;
an eyebrow embroidery needle module, having a core link rod installed at an end of the eyebrow embroidery needle module, an eyebrow embroidery needle installed at another end of the eyebrow embroidery needle module and wherein the eyebrow embroidery needle module includes a needle bushing having a substantially H-shaped axial cross-section, and the core link rod is installed at an end of the needle bushing, and the eyebrow embroidery needle is installed at another end of the needle bushing;
an anti-backflow plastic cover, made of an elastic material, and having an end sheathed and fixed onto the periphery of the eyebrow embroidery needle module, and a flange at another end abutted against the protruding rib proximate to a side of the internal screw thread, such that the eyebrow embroidery needle module is installed in the connecting sleeve, and the eyebrow embroidery needle passes through the eyebrow embroidery bushing and extends to the outside from another end of the eyebrow embroidery bushing;
a transmission mechanism, having a motor installed therein, and an external screw thread formed at an end outside the transmission mechanism and screwed and engaged with the internal screw thread of the connecting sleeve, and a transmission rod of the motor being coupled to the core link rod, such that the core link rod, the anti-backflow plastic cover and the eyebrow embroidery needle can be moved reciprocally along a central axis of the eyebrow embroidery machine; and at least one watertight O-ring installed to the flange at the another end of the anti-backflow plastic cover and proximate to the side of the internal screw thread, such that the watertight O-ring and the flange at the another end of the anti-backflow plastic cover are forcedly pressed between the protruding rib and the transmission mechanism to define a watertight status.

2. The eyebrow embroidery machine of claim 1, wherein the transmission rod has a magnet installed at an end of the transmission rod, and the core link rod has a metal nugget installed at an end of the core link rod, and the magnet and the metal nugget are attracted with each other.

3. The eyebrow embroidery machine of claim 1, wherein the transmission rod has a metal nugget installed at an end of the transmission rod, and the core link rod has a magnet installed at an end of the core link rod, and the magnet and the metal nugget are attracted with each other.

4. The eyebrow embroidery machine of claim 1, wherein the transmission rod has a first magnet installed at an end of the transmission rod, and the core link rod has a second magnet installed at an end of the core link rod, and the first magnet and the second magnet are attracted with each other.

5. The eyebrow embroidery machine of claim 2, wherein the circular flange and the eyebrow embroidery bushing are integrally formed as a whole.

6. The eyebrow embroidery machine of claim 3, wherein the circular flange and the eyebrow embroidery bushing are integrally formed as a whole.

7. The eyebrow embroidery machine of claim 4, wherein the circular flange and the eyebrow embroidery bushing are integrally formed as a whole.

* * * * *